United States Patent
Te Hennepe et al.

(10) Patent No.: US 6,989,166 B2
(45) Date of Patent: Jan. 24, 2006

(54) SOFT DRINK REPLACER

(75) Inventors: Frederik Gerhard Johan Te Hennepe, Wageningen (NL); Maria Elisabeth Hermien De Lange, Wageningen (NL); Katrien Maria Jozefa Van Laere, Heteren (NL); Peter Antonio Navarro Y Koren, Ede (NL)

(73) Assignee: N.V. Nutricia, Zoetermeer (NL)

( * ) Notice: Subject to any disclaimer, the term of this patent is extended or adjusted under 35 U.S.C. 154(b) by 195 days.

(21) Appl. No.: 10/279,968

(22) Filed: Oct. 25, 2002

(65) Prior Publication Data

US 2003/0134027 A1 Jul. 17, 2003

Related U.S. Application Data

(63) Continuation-in-part of application No. 10/022,372, filed on Dec. 20, 2001.

(30) Foreign Application Priority Data

| Jun. 7, 2002 | (EP) | 02077222 |
| Oct. 16, 2002 | (EP) | 02079289 |

(51) Int. Cl.
*A23L 2/00* (2006.01)

(52) U.S. Cl. .......................... 426/2; 426/590; 426/575; 426/577

(58) Field of Classification Search .................. 426/2, 426/590, 575, 578, 577, 567, 74; 424/439; 514/909–911
See application file for complete search history.

(56) References Cited

U.S. PATENT DOCUMENTS 6,187,334 B1 * 2/2001 Yamagata et al. .......... 424/439

FOREIGN PATENT DOCUMENTS

| JP | 07-067575 | 3/1995 |
| JP | 07-069902 | 3/1995 |
| WO | WO 96/33694 | 10/1996 |

OTHER PUBLICATIONS

S. Bagheri, L. Gueguen, "Effect of wheat bran and pectin on the absorption and retention of phosphorus, calcium, magnesium and zinc by the growing pig.", Reprod. Nutr. Develop., 1985, 24 (4A), 705–716.

Translation from Japanese, Tables 11 and 12.

* cited by examiner

*Primary Examiner*—Carolyn Paden
(74) *Attorney, Agent, or Firm*—Young & Thompson

(57) ABSTRACT

The present invention relates to a method for the treatment and/or prevention of overweight in a monogastric mammal. More particularly, the invention is concerned with such a method comprising administering to the mammal a liquid edible composition with a pH of more than 5, a viscosity below 50 mPas at a shear rate of $100s^{-1}$ and 20° C., and a viscosity of at least 125% of the aforementioned viscosity at a pH 3 and a temperature of 37° C.; and with a caloric density between 0 and 500 kcal per liter, the composition comprising: between 0.01 and 5 wt. % of one or more polysaccharides selected from the group consisting of pectin and alginate; and between 0.01 and 3 wt. % calcium

20 Claims, 4 Drawing Sheets

Figure 1a: Average rating in time for the question "Are you hungry"
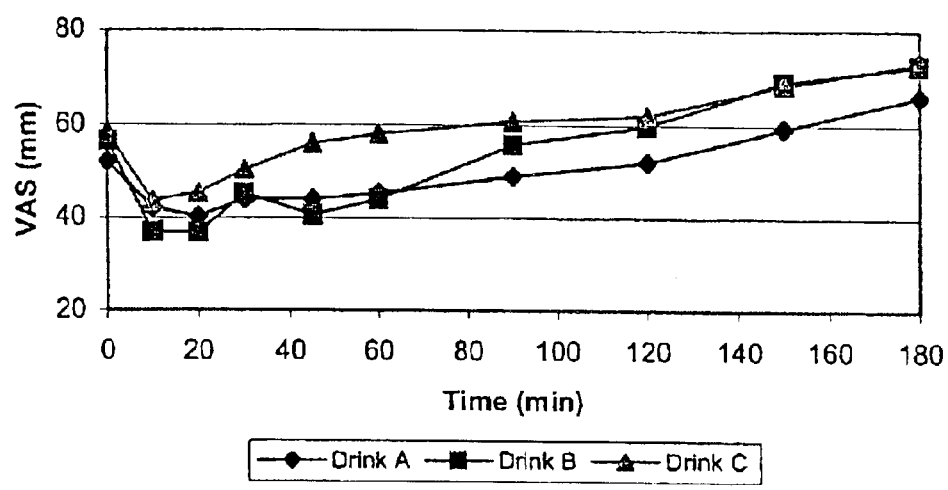
Figure 1b: AUC for the question "Are you hungry"
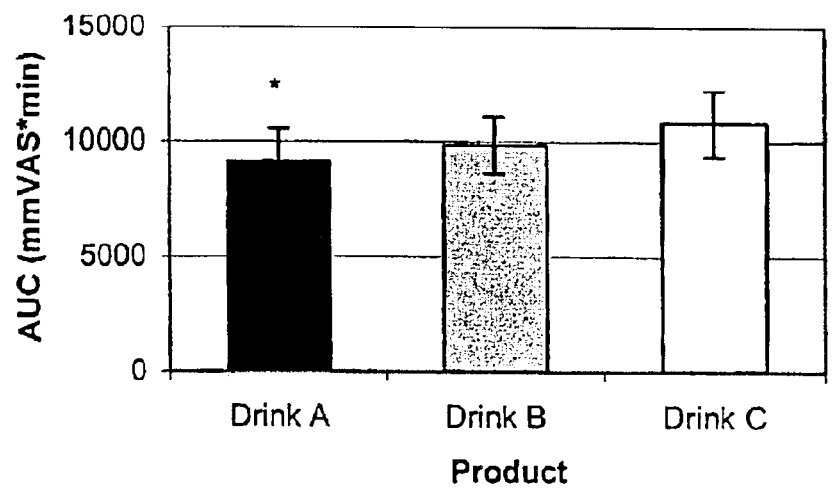

Figure 2a: Average rating in time for the question "Appetite for food"
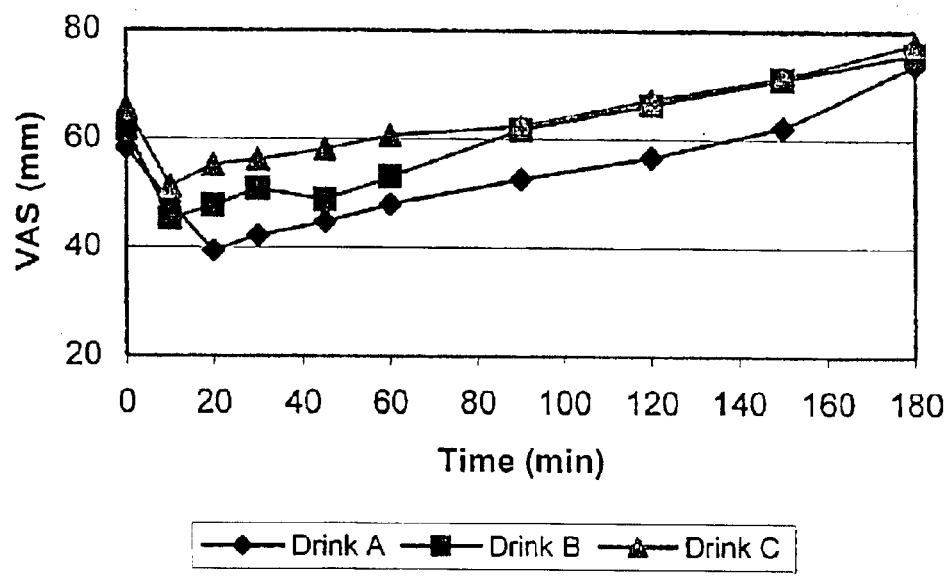
Figure 2b: AUC for the question "Appetite for food"
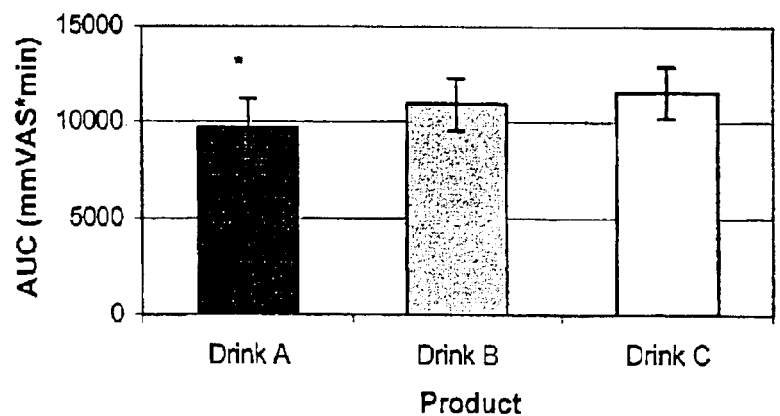

Figure 3a: Average rating in time for the question "How much could you eat"
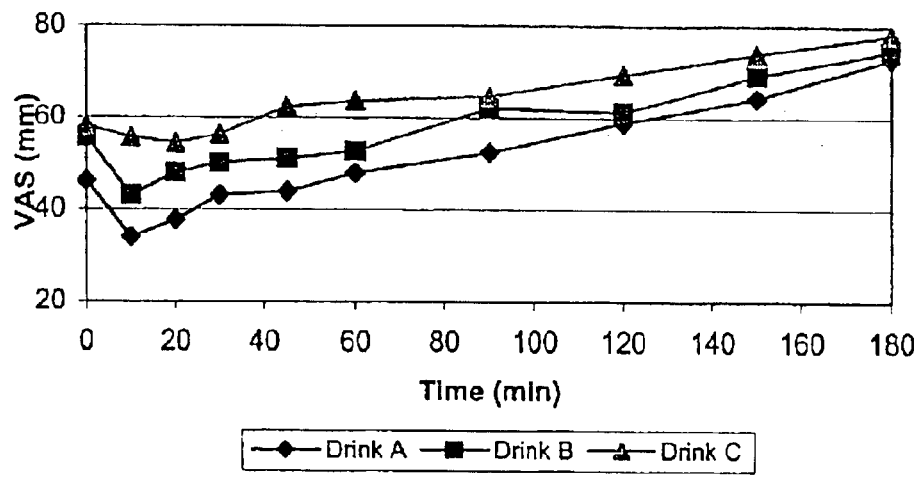
Figure 3b: AUC for the question "How much could you eat"
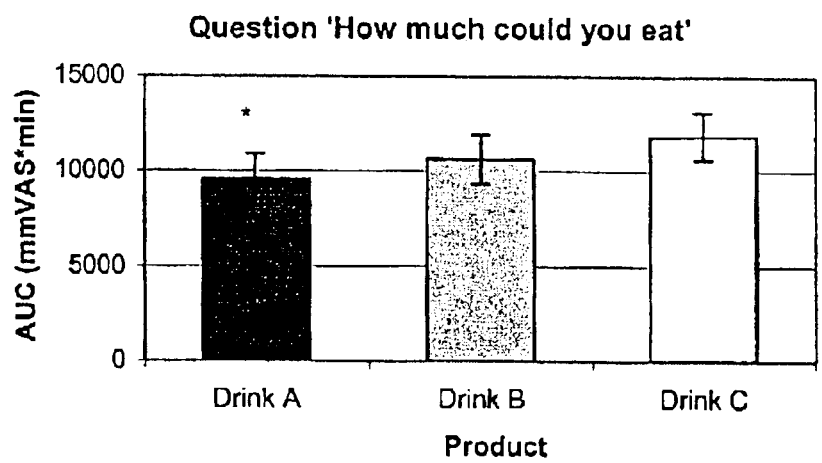

Figure 4a: Average rating in time for the question "Are you thirsty"
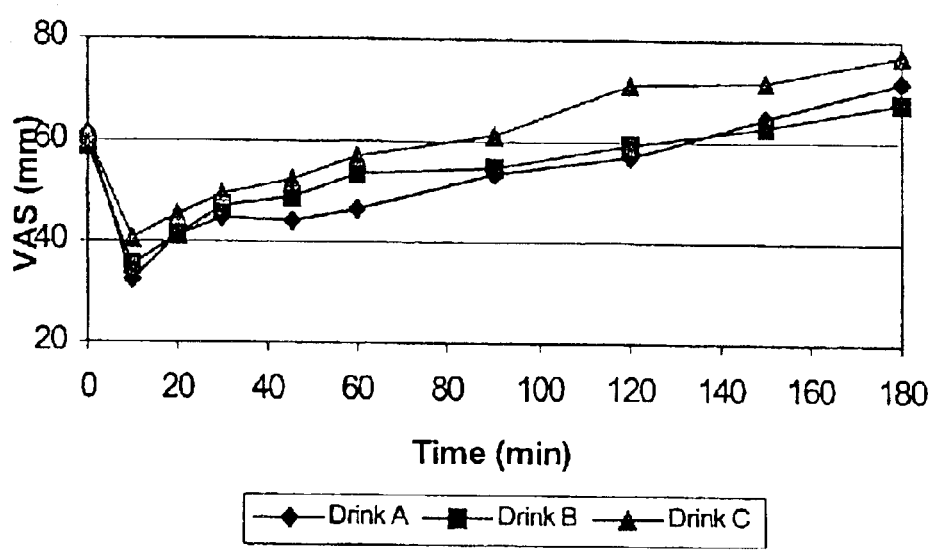
Figure 4b: AUC for the question "Are you thirsty"
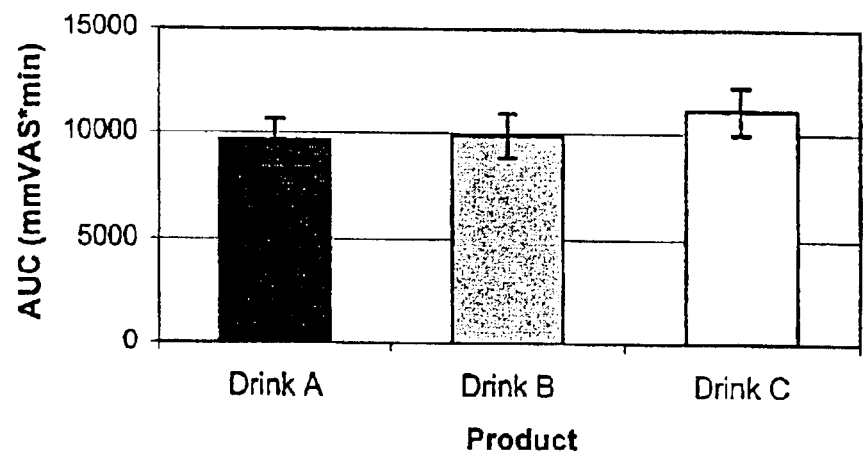

SOFT DRINK REPLACER

This application is a continuation-in-part of co-pending application Ser. No. 10/022,372, filed on 20 Dec. 2001, the entire contents of which are hereby incorporated by reference.

FIELD OF THE INVENTION

The present invention relates to a method for the treatment and/or prevention of overweight, said method comprising administering to a monogastric mammal a pectin and/or alginate containing liquid composition.

STATE OF THE ART

In effect, overweight in mammals is caused by the ingestion of excess calories. Calories are for example ingested via high caloric meals. Within the art, several strategies are known for reducing caloric intake. These strategies include for example replacing the high caloric meals by low caloric meals (e.g. meal replacers) or the ingestion of medicaments that reduce the absorption of high caloric components from the meal (e.g. lipase inhibitors).

Presently, a major contributor to the daily caloric intake are soft drinks. For example, in the USA, the ingestion of sugars from soft drinks presently is about 36.2 grams daily for adolescent girls and 57.7 grams for boys. These figures approach or exceed the daily limits for total added sugar consumption recommended by the USDA. Hence, the soft drink consumption has been related to the incidence of obesity, particular in school children.

The US National Institute of Health has been recommending that people who are trying to lose or control their weight should drink water instead of sugar containing soft drinks. However, water consumption remains minimal, even by subjects suffering from overweight.

A further low caloric alternative for sugar containing soft drinks are the so called "diet" or "light" soft drinks. Although an interesting alternative for sugar containing soft drinks, the "light" and "diet" soft drinks suffer from bad acceptance. Additionally, these drinks generally contain high quantities of phosphoric acid. The high levels of phosphoric acid in these "diet" soft drinks have undesirable side effects. Phosphoric acid can combine with calcium and magnesium in the gut to cause a loss of these vital minerals. This is particularly undesirable if it is consumed by subjects wishing to prevent or reduce overweight, since calcium contributes to the maintenance of a healthy body weight (Zemel et al; J Am Coll Nutr 2002 April; 21(2):146S–151S). Furthermore, reduced bioavailability of calcium is particularly undesirable for adolescents, for obvious reasons.

U.S. Pat. No. 6,248,390 (Stillmann) discloses a water composition containing soluble indigestible fiber. The water composition comprises between 0.1% and 10% by weight of water-soluble indigestible fiber, wherein fewer that 10 calories per 100 ml is metabolised by a human when consuming the composition. The soluble fibre may be selected from the group consiting of plant mucilage, plant gums, dextrins, maltodextrins, galactomannans, arabanogalactans, beta glucans, cellulose ethers, pectins, pectic material, water-soluble hemicellulose, inulin, alginates, agar, carrageenan, psyllium, guar gum, gum traganth, gum karya, gum ghatti, gum acacia, gum arabic, partially hydrolyzed products thereof and mixtures thereof.

EP493265 (Iwata et al) relates to an algin-containing food or beverage comprising a low-molecular weight algin which has a weight-average molecular weight in the range of 10,000–900,000 and still functions as a dietary fiber and has beneficial effects on the health.

The currently known low caloric drinks all have the disadvantage that they do not sufficiently mimic the physiological effects of a sugar containing soft drink. This results in a low consumer acceptance in large groups of overweight soft drink users. Hence, there is an unmet need for low caloric drinks that can advantageously be used for replacing sugar containing soft drinks as they produce a physiological effect that closely resembles the physiological effects of sugar containing soft drinks, e.g. in that they induce satiety.

In order to be suitable for soft drink replacement, a low caloric drink should ideally meet a number of different criteria:

Naturally, the soft drink replacer needs to have low caloric density to make it suitable for treatment or prevention of overweight.

Also, the drink needs to have low viscosity. Low viscosity is of importance for acceptance of the product. Low viscosity is of additional importance as it enables consumption of large quantities.

Furthermore, the soft drink replacer needs to have good palatability. Bad palatability results in reduced acceptance of the drink, reducing its effective use in a method for the reduction or prevention of overweight.

A soft drink replacer preferably should provide a mouthfeel that is very similar to the mouthfeel of a sugar containing soft drink.

Finally, the soft drink replacer needs to have a good thirst quenching effect.

SUMMARY OF THE INVENTION

The present inventors have developed a liquid composition that can suitably be used as a soft drink replacer. Hence, the present liquid composition can suitably be used in a method for the prevention or treatment of overweight. It was found that a low caloric drink comprising between 0.01 and 5 wt. % pectin and/or alginate and between 0.01 and 3 wt. % insoluble calcium salt provides a beverage with acceptable viscosity, acceptable palatability, good thirst quenching effects and low caloric density.

Simple addition of calcium to a pectin containing drink is disadvantageous, since it leads to an unacceptable high viscosity of the composition. For example, the drink as decribed in JP11206351 contains both pectin and calcium however has a viscosity of between 800 and 3000 mPas. Such high viscosity will result in low consumer acceptance, unacceptable mouth-feel and reduced fluid replenishment. It was surprisingly found that the present liquid composition is capable of reducing the appetite. This was unexpected. Drinks containing pectin and calcium and high amounts of glucose have been described to reduce the postprandial mean peak in serum glucose (Wolf et al, 2002; Nutrition 18:621–626). Low caloric drinks containing pectin and calcium have been described in the art as a support for medicaments (WO9959542). However, from these disclosures it cannot be concluded that the present low caloric liquid composition has an appetite reducing effect.

It was found that the present liquid composition mimics the physiological and organoleptic properties of sugar containing soft drinks. Due to the low viscosity of the present drink, it mimics the organoleptic properties of water and soft drinks, which ensures a sufficient hydration and good acceptance. However, when ingested, the drink reaches the stomach where it forms a matrix under the acidic conditions of the stomach. Without wishing to be bound by theory, it is the inventors believe that the formation of a viscous matrix in the stomach increases the release of cholecystokinin (CCK), thereby inducing the feeling of satiety. Hence the present drink comprises a substantial improvement over the presently known drinks that aim to replace sugar containing soft drinks.

Furthermore, it was surprisingly found that the present drink has good thirst quenching properties. A good thirst quenching effect is of great importance for the consumer acceptance of soft drinks and replacers for such soft drinks.

BRIEF DESCRIPTION OF THE DRAWINGS

FIG. 1a shows the results of the tests for average visual analog score (VAS) over time for question "Are you hungry?" FIG. 1b shows the shows the results in terms of the specific area under the curve (AUC) for three test drinks.

FIG. 2a shows the results of the tests for VAS over time for the question as to "Appetite for food". FIG. 2b shows the results in terms of AUC for three test drinks.

FIG. 3a shows the results of the tests for VAS over time for the question as to "How much could you eat?". FIG. 3b shows the results in terms of AUC for three test drinks.

FIG. 4a shows the results of the tests for VAS over time for the question as to "Are you thirsty?". FIG. 4b shows the results in terms of AUC for three test drinks.

DETAILED DESCRIPTION

The present invention relates to a method for the treatment or prevention of overweight in a monogastric mammal comprising administering to the mammal a liquid edible composition with a pH of more than 5, a viscosity below 50 mPas at a shear rate of 100 s$^{-1}$ and 20° C., and a viscosity of at least 125% of the aforementioned viscosity at a pH 3 and a temperature of 37° C. and which has a caloric content between 0 and 500 kcal/liter, the composition comprising:

a) between 0.01 and 5 wt. % of pectin and/or of alginate; and b) between 0.01 and 3 wt. % calcium Pectin Pectins are carbohydrates generally obtained from dilute acid extracts of citrus or apple pulp. They are also present in the cellular walls of vegetables and fruits. Pectins are also found in root crops such as carrots and beetroot, as well as in tubers, such as potatoes. It is commercially extracted from citrus peels, apple pomace and sugar beet pulp. A typical pectin molecule comprises 200 to 1000 galacturonic acid units connected in a linear chain. The drink used in the present method preferably contains water-soluble pectin.

Pectin is divided into two main categories: high methoxylated pectin (hereafter referred to as HM pectin), which are characterized by a degree of methoxylation above 50% and low methoxylated pectin (hereafter referred to as LM pectin) having a degree of methoxylation below 50%. As used herein, "degree of methoxylation" (also referred to as DE or "degree of esterification") is intended to mean the extent to which free carboxylic acid groups contained in the polygalacturonic acid chain have been esterified (e.g. by methylation).

LM pectins are further subdivided into two groups: low methoxylated amidated, and low methoxylated conventional. As used herein the "degree of amidation" (DA) is intended to mean the extent to which ester groups contained in the polygalacturonic acid chain have been converted to amide groups by reaction with e.g. an ammonium hydroxide in solution.

The LM pectins are preferably used in the present invention. LM pectins are characterized by a degree of methoxylation below 50%, preferably between 5% and 45%, more preferably between 10% and 40%, even more preferably between 15% and 35%. According to a further preferred embodiment, the LM pectins are amidated, the degree of amidation preferably being below 30%, preferably below 25%, even more preferably below 20%. The preferred lower limit of the degree of amidation is 5%, more preferably 10%.

LM pectins are advantageously used since, in combination with calcium, they are capable of forming a sufficiently rigid matrix at a pH found in the stomach of a normal human, e.g. pH 3. However, pectin cannot be included unrestrictedly in the drink, since at high concentrations the composition will acquire an unacceptable high viscosity. Hence the liquid composition used in the present method contains less than 5 wt. %, preferably less than 4 wt. %, even more preferably less than 2.5 wt. %, most preferably less than 1.5 wt. % pectin based on the total weight of the liquid composition.

On the other hand, a significant concentration of pectin is required to provide a satiety inducing effect. Hence, the present liquid composition preferably includes at least 0.01 wt. %, preferably at least 0.1 wt. %, more preferably at least 0.25 wt. % pectin, even more preferably at least 0.5 wt. % pectin based on the total weight of the liquid composition.

Alginate

Alginates are linear unbranched polymers containing β-(1→4)-linked D-mannuronic acid and α-(1→4)-linked L-guluronic acid residues with a wide range of average molecular weights (100–100000 residues). Suitable sources of alginate include seaweeds and bacterial alginates. Preferably sodium alginate and potassium alginate are used as a source of alginate.

However, alginate cannot be included unrestrictedly, since at high concentrations the composition will acquire an unacceptable high viscosity. Hence the liquid composition used in the present method contains less than 5 wt. %, preferably less than 4 wt. %, even more preferably less than 2.5 wt. %, most preferably less than 1.5 wt. % alginate based on the total weight of the liquid composition.

On the other hand, a significant concentration of alginate is needed to provide a satiety inducing effect. Hence, the present liquid composition preferably includes at least 0.01 wt. %, preferably at least 0.1 wt. %, more preferably at least 0.25 wt. %, and even more preferably at least 0.5 wt. % alginate based on the total weight of the liquid composition.

In a preferred embodiment the present composition contains pectin, even more preferably LM pectin.

Calcium

Calcium is essential in a diet and of key relevance in the prevention and/or treatment of overweight (see Zemel et al, 2002, J Am Coll Nutr April; 21(2):146S–151S). Additionally calcium deficiency may cause osteoporosis, muscle cramps, eczema, aching joints, increased cholesterol levels, rheumatoid arthritis and tooth decay. However, calcium and pectin form a rigid matrix when brought together in a solution. Hence the skilled man would not be motivated to use calcium in combination with pectin and/or alginate, particularly low methoxylated pectin, in a drink aimed to replace soft drinks.

The composition used in the present invention contains a calcium salt, which is substantially less soluble in water at 20° C. and at the pH of the present composition than at 37° C. and a pH below 5. Such a calcium salt, when present in the composition in an amount that exceeds its maximum solubility, will dissolve in the stomach under the influence of pH-reduction and/or temperature increase. Thus the calcium ion concentration in the composition will increase, which will automatically stimulate pectin and/or alginate gellation.

Because of the gellation inducing effect of calcium ions, the concentration of such ions in the present liquid composition (at near neutral pH) is preferably relatively low. The limited presence of (dissolved) calcium ions at around neutral pH prevents the formation of a gel matrix which would impart unacceptably high viscosity. Thus, in a preferred embodiment, the calcium salt(s) used in the present composition have a solubility below 0.15, more preferably below 0.1, even more preferably below 0.06 gram per 100 ml (demineralised) water at 20° C. and pH 7. Preferably, the calcium salt(s) provide more than 0.2 gram dissolved calcium per 100 ml water at a pH below 5 and a temperature of 37° C., more preferably it provides more than 0.5 g per 100 ml water under these conditions. The solubility of the calcium salt at pH below 5 and at 37° C. is not bound to an upper limit, however, is typically below 500 g of the salt per 100 ml water.

The calcium salt is preferably selected from the group consisting of calcium phosphate (e.g. tribasic, dibasic, monobasic or penta calcium triphosphate), calcium carbonate, calcium sulfate, calcium oxide, calcium citrate (e.g. mono-calcium citrate or tri-calcium citrate), a calcium salt coated with a substance which has limited solubility in water at pH 7 and is soluble at a pH below about 5 (hereafter referred to as coated calcium salts) and mixtures thereof. Examples of coatings and methods for the preparations of coated calcium salts are given in WO0038829, the entire content of which is hereby incorporated by reference.

More preferably, the calcium salt is selected from the group consisting of coated calcium salt, calcium carbonate and mixtures thereof. Even more preferably between 50 wt. % and 100 wt. % of calcium salt is provided as calcium carbonate.

To provide optimal gelling characteristics without significantly effecting the palatability of the present liquid composition, the composition according to the invention preferably contains less than 3 wt. % calcium salt, more preferably less than 1 wt. % calcium salt, even more preferably less than 0.5 wt. % calcium salt, most preferably less than 0.2 wt. % calcium salt based on the total weight of the drink. In a further preferred embodiment, the present liquid composition contains at least 0.005 wt. % calcium salt, more preferably at least 0.01 wt. % calcium salt, even more preferably at least 0.02 wt. % calcium salt.

The liquid composition preferably contains at least 25 mg Ca per liter. Preferably the calcium concentration exceeds 50 mg Ca per liter, more preferably it exceeds 100 mg Ca per liter, most preferably it exceeds 150 mg Ca per liter. Furthermore, the calcium concentration in the composition preferably does not exceed 15 gram Ca per liter, more preferably it does not exceed 5 gram Ca per liter, even more preferably it does not exceed 3 gram Ca per liter.

The calcium concentration in the composition may be determined by first completely solubilising the calcium, followed by the determination of the calcium concentration. The majority of the calcium will be present in the drink as a calcium complex and/or insoluble calcium salt when the composition is at neutral pH and thus unavailable to form a viscous matrix with the LM pectins. At a pH between 1 and 5, the calcium will mostly be in a solubilized form and/or be present as a pectin-calcium complex. For determination of the calcium content of the present drink, all calcium, i.e. the solubilized, insoluble and the calcium present in complexes, needs to be taken into account.

Viscosity

Advantageously the viscosity of the liquid composition used in the present method is below 50 mPas, more preferably below 40 mPas, even more preferably below 25 mPas, even more preferably below 10 mPas, most preferably below 5 mPas at a shear rate of 100 s$^{-1}$ and 20° C. At pH 3 and 37° C. the composition has a viscosity which is at least 125% of the aforementioned viscosity at near neutral pH, more preferably above 150%. According to a further preferred embodiment the liquid edible composition at pH 3 and at 37° C. has a viscosity of at least twice the viscosity of the composition at pH 7 and 20° C., preferably at least thrice. Preferably, the present liquid composition has a viscosity at pH 3 and 37° C. which exceeds 100 mPas, more preferably exceeds 250 mPas, most preferably exceeds 1000 mPas at a shear rate of 100 s$^{-1}$. Preferably, the viscosity of the composition at pH 3 and 37° C. does not exceed 100,000 mPas at a shear rate of 100 s$^{-1}$.

Whenever the term viscosity is used in the present document, this refers to the physical parameter which is determined according to the following method:

The viscosity may be determined using a Carri-Med CSL rheometer. The used geometry is of conical shape (6 cm 2 deg acrylic cone) and the gap between plate and geometry is set on 55 μm. A linear continuous ramp shear rate is used from 0 to 150 s$^{-1}$ in 20 seconds. The rheometer's thermostat is set on the appropriate temperature (e.g. 20° C. or 37° C.). In order to determine the viscosity at acidic pH (pH 3), first a sufficient amount of 1 M HCl is homogeneously admixed (drop-wise under very gentle stirring for about 20 sec, to prevent the breakdown of the gel) to the liquid composition to adjust the pH of the composition to pH 3. Thereafter the composition is left standing at 20° C. for about 10 minutes. Subsequently the composition thus obtained is used to determine the viscosity at pH 3, according to the method described above.

Caloric Content

It is an essential feature of the present invention that the liquid composition used in the present method contains between 0 and 500 kcal per liter. Advantageously, the liquid composition has a caloric density below 400 kcal per liter, even more preferably below 250 kcal per liter, most preferably below 50 kcal per liter, particularly below 25 kcal per liter.

A unit dosage of the present drink preferably contains between 0 and 100 kcal, more preferably between 0 and 50 kcal, even more preferably between 0 and 40 kcal, most preferably between 0 and 25 kcal, particularly between 0 and 10 kcal.

The caloric content of an edible composition can be suitably calculated by multiplying the caloric density of an ingredient per gram with the weight of the ingredient included in the composition. The cumulative value gives the caloric content of the edible composition. The caloric content of protein is approximately 4 kcal per gram, fat contains approximately 7 kcal per gram, digestible carbohydrate contains approximately 4 kcal per gram, and indigestible fermentable ingredient contains about 1.5 kcal per gram.

Thinners

To decrease the viscosity of the present composition (at near neutral pH), polyols may be advantageously added, Preferably the added polyols are selected from the group consisting of xylitol, sorbitol, maltitol, mannitol, erythritol and or mixtures thereof. In a preferred embodiment mannitol is used. Preferably these viscosity decreasing ingredients are added in an amount of 0.5 to 3 wt. % based on the total weight of the drink. Suitable examples of the use of polyols in the present drink are given in WO0038829, the entire content of which is hereby incorporated by reference.

According to another embodiment of the invention the present composition may additionally comprise an anion selected from the group consisting of citrate, phosphate and mixtures thereof. These anions form a complex or insoluble salt with calcium at pH 7. However, inclusion of the anions, e.g. though incorporation of a soluble (mineral) salt, reduces the palatability of the drink. Hence the drink preferably contains less than 2 wt. %, preferably less than 1 wt. %, even more preferably less that 0.5 wt. %, most preferably less than 0.1 wt. % of a salt selected from the group consisting of potassium or sodium salt of citrate or phosphate.

A problem with pectin and calcium containing drinks is the limited shelf life of such products. It was surprisingly found that the present composition has a good shelve life. Hence, in a preferred embodiment the viscosity of the present liquid edible composition after incubating the composition a period of 60 days (at 20° C.) is below 300% of the starting viscosity, more preferably below 200%, even more preferably below 150%. The starting viscosity may be determined before the drink has reached equilibrium, for example directly after manufacturing of the liquid composition. It was found that the favorable characteristics of the present drink are not significantly altered during sterilization. Hence, advantageously, the present method comprises the administration of a sterilized liquid composition drink.

Solid/Liquid Forms

Advantageously, the present drink is reconstituted from a powder, tablet or concentrated liquid that contains the pectin and/or alginate and calcium salt by mixing the reconstitutable preparation with a predetermined amount of water. Alternatively, the present composition may also be provided in a ready-to-drink form (i.e. liquid form), which can be consumed without the need for further preparation, i.e. does not require the addition of liquid before ingestion.

For easy manufacturing and/or to provide easy handling by the consumer (e.g. limiting weight for convenience), the drink may advantageously be provided as a reconstitutable preparation, more preferably in the form of a reconstitutable preparation accompanied with instructions to reconstitute the preparation into a suitable liquid, preferably water, prior to consumption. The term "reconstitutable preparation" as used herein refers to a preparation that needs addition of a suitable liquid prior to ingestion.

The present method preferably comprises the administration of a unit dosage of the present drink. Advantageously, a unit dosage of the liquid composition has a volume of at least 25 ml, more preferably at least 50 ml, even more preferably at least 100 ml of the composition. Preferably a unit dosage does not exceed 2000 ml, more preferably does not exceed 1000 ml, even more preferably does not exceed 500 ml, most preferably does not exceed 400 ml. Hence, a unit dosage may be a packaged liquid beverage which has a volume within one or more of the above ranges, or a reconstituted preparation which has a volume within one of the above ranges. For consumer convenience, the reconstitutable preparation is preferably accompanied with instructions for mixing a predetermined amount of powder, tablets or reconstitutable liquid with a predetermined volume of liquid. Preferably, the present method comprises the administration of a ready-to drink formula. The term "ready-to-drink" as used herein refers to a packaged preparation that does not need mixing with a liquid prior to ingestion.

If a reconstitutable preparation or ready-to drink formula is packaged in a form containing multiple unit dosages, it is preferably accompanied with indicia which describe the method for separating one unit dosage from the bulk and/or portion identification aids such as measuring devices for determining portion size.

When the present composition is supplied in powder form, it is preferably accompanied with instructions to consume the product within 60 minutes, preferably within 30 minutes after reconstitution.

Limited Amounts of Other Ingredients

In order for the present liquid composition to combine a low viscosity with a low caloric content and high translucency it is preferred to include no more than a limited amount of other ingredients. Hence, preferably the present composition contains:

less that 1 wt. % protein based on the total weight of the drink, preferably less than 0.1 wt. %, more preferably less than 0.01 wt. %; and/or less than 1 wt. % glycerides (i.e. tri-, di- and/or monoglycerides) and/or fatty acids based on the total weight of the drink, preferably less than 0.1 wt. %, more preferably less than 0.01 wt. %; and/or less than 3 wt. % digestible carbohydrates based on the total weight of the drink, preferably less than 1 wt. %, more preferably less than 0.5 wt. %.

Increased transparency of the drink contributes to the acceptance to the drink.

Advantageously, the dry solids content of the drink does not exceed 100 grams per liter, preferably does not exceed 75 grams per liter, more preferably does not exceed 50 grams per liter, even more preferably does not exceed 25 grams per liter. In a particularly preferred embodiment at least 25 wt. %, more preferably at least 50 wt. %, even more preferably at least 75 wt. % of the dry solids of the liquid composition is water-soluble indigestible fiber, preferably water-soluble indigestible fiber selected from the group consisting of pectin, alginate, indigestible water soluble oligosaccharide and mixtures thereof, even more preferably pectin.

According to a further preferred embodiment at least 95 wt. %, preferably at least 96.5 wt. %, even more preferably at least 98 wt. %, most preferably at least 99 wt. % of the liquid composition consists of water, pectin and/or alginate, calcium saltand, if present, indigestible fermentable ingredient.

Low Caloric Sweetener and Flavor

To increase the palatability of the present liquid composition without substantially increasing the caloric content of the composition, low caloric sweetener and/or flavor are advantageously added. The composition preferably contains at least one food grade flavor, preferably citrus flavor.

According to a preferred embodiment the present liquid edible composition comprises a low caloric sweetener. The low caloric sweetener preferably has a caloric density below 3 kcal per gram, preferably below 2 kcal per gram, even more preferably below 1 kcal per gram. The low caloric sweeter preferably is selected from the group consisting of indigestible oligosaccharides, polyols, aspartame, sucralose, acesulfame potassium, alitame, cyclamate, saccharin, tagatose and mixtures thereof. Preferably, the low caloric sweetener does provide less than 10 kcal, more preferably less than 5 kcal, even more preferably less than 2 kcal per liter of the present drink. Advantageously the present drink contains less than 1 wt. % even more preferably less than 0.5 wt. % low caloric sweetener, even more preferably less than 0.1 wt. % low caloric sweetener.

To achieve good consumer acceptance, the liquid composition preferably has a sucrose equivalent value (SEV) of at least 0.2, preferably at least 0.5, even more preferably at least 1 SEV. Preferably the SEV is below 25, more preferably below 10, even more preferably below 5.

Bottom Sedimentation

Advantageously the drink contains an ingredient that is capable of reducing bottom sedimentation. Bottom sedimentation is undesirable, since it reduces palatability and decreases the appetite reducing properties of the drink. Preferably the ingredient capable of reducing bottom sedimentation is selected from the group consisting of carrageenan, gum arabic, xanthane gum and mixtures thereof. More preferably,-carrageenan is used. Since these ingredients contribute to an increased viscosity, the present drink preferably contains between 0 and 0.1 wt. %, more preferably between 0.005 and 0.1 wt. % of such an ingredient that is capable of reducing bottom sedimentation, based on the total weight of the present drink.

Transparency

Advantageously, the present drink has an absorbance of below 0.5, preferably below 0.25, even more preferably below 0.2, most preferably below 0.17 when measured by using a spectrophotometer at 620 nm (cell thickness of 1 cm). Absorbance of water as a blank is set at 0. Decreased absorbance (i.e increased transparency) of the drink contributes to the acceptance of the drink.

Indigestible Fermentable Ingredient

The present liquid composition can be even further improved, making it particularly suitable for use in a method for the treatment or prevention of overweight by increasing the calcium bioavailability of the present drink. It was found by the present inventors that bioavailability of calcium from the present drink could be improved through the coadministration of an indigestible fermentable ingredient.

It was found by the present inventors that compositions providing a satiety effect through the gellation of pectin and/or alginate significantly reduce calcium absorption and/or bioavailability. Also it was found by the inventors that the calcium absorption inhibitory effect of pectins and/or alginate (particularly low methoxylated pectins) present in the drink can be decreased effectively through the coadministration of indigestible ingredient that can be fermented by intestinal bacteria.

Without wishing to be bound by theory, it is the inventors believe that the indigestible fermentable ingredient provides a readily metabolisable substrate for the intestinal flora. Ingestion of indigestible fermentable ingredients will result in an increase of the mass of intestinal bacteria (particularly bifidobacteria and/or lactobacilli) and/or increase the activity of these bacteria, and thereby stimulate the degradation of the pectin matrix. Through the stimulated breakdown of the pectin and/or alginate matrix in the small intestine and colon, the calcium bioavailability increases through resulting release of the pectin bound calcium. Still the pectins and/or alginates will have provided the desired satiety inducing effect through the formation of a viscous matrix in the stomach and/or intestine.

Additionally, the fermentation of the indigestible fermentable ingredient by the intestinal bacteria will yield lactate and/or short chain fatty acids (SCFA), including butyrate, propionate and acetate, resulting in a decreased pH in the colon, which increases mineral solubility, hence raises the concentration of ionized calcium and accelerates the passive diffusion of calcium. Additionally, SCFA may be responsible for a rise in caecal blood flow and consequently increased mineral absorption.

Furthermore, the indigestible fermentable ingredient may stimulate intestinal calcium transport by hypertrophy of the caecal wall, thereby increasing the surface area where mineral exchange takes place, thus improving calcium absorption.

Hence the present method advantageously encompasses the administration of a liquid composition comprising an indigestible fermentable ingredient other than pectin and/or alginate, more preferably an indigestible fermentable fiber other than pectin and/or alginate, even more preferably a water-soluble indigestible fermentable fiber other than pectin and/or alginate. Preferably the indigestible fermentable ingredient is selected from the group consisting of indigestible oligosaccharides, polyols and mixtures thereof. Indigestible oligosaccharides is the preferred water-soluble indigestible fermentable fiber. The term indigestible oligosaccharides as used in the present invention refers to saccharides which have a degree of polymerisation of monose units exceeding 2, more preferably exceeding 3, most preferably exceeding 4, which are not or only partially digested in the intestine by the action of acids or digestive enzymes present in the human upper digestive tract (small intestine and stomach) but which are fermented by the human intestinal flora. The degree of polymerisation of the oligosaccharide is below 60 monose units, preferably below 40, even more preferably below 20, most preferably below 10. The term monose units refers units having a closed ring structure, preferably hexose, particularly the pyranose or furanose forms. According to a preferred embodiment the oligosaccharide is selected from the group consisting of fructans, fructooligosaccharides, indigestible dextrins, galactooligosaccharides (including transgalactooligosaccharides), xylooligosaccharides, soybean oligosaccharides, arabinooligosaccharides, glucooligosaccharides, mannooligosaccharides, fucooligosaccharides and mixtures thereof.

The term polyols refers to chemical derivatives of sugars that differ from the parent compounds in that aldehyde groups (CHO) have been replaced by an alcohol group ($CH_2OH$). Polyols are more commonly referred to as sugar alcohols. Preferably the polyol selected from the group consisting of sorbitol, erythritol, maltitol, mannitol, isomalt, xylitol and mixtures thereof.

Preferably the present drink comprises between 0.01 and 15 wt. %, more preferably between 0.1 and 10 wt. %, even more preferably 0.5 and 10 wt. % indigestible fermentable ingredient based on the total weight of the liquid composition. The indigestible fermentable ingredient may be the same ingredient used for sweetening the drink. For determining the weight percentage indigestible fermentable ingredient in the present composition, the weight percentage of all ingredients other than pectin and/or alginate that can be considered indigestible fermentable ingredients have to be added up, irrespective of the functionalities of the ingredient.

The indigestible fermentable ingredient used in the present drink is preferably capable of significantly increasing the total cecal and/or colonic SCFA content. According to a preferred embodiment of the invention, the ingredient, when administered in a sufficient amount, is capable of increasing total cecal SCFA content by at least 20%, compared to a composition wherein the fermentable ingredient is absent, more preferably at least 50%, even more preferably at least 100%, most preferably at least 150%. The increase of total cecal SCFA content can be determined according to the method described by Campbell et al.(The Journal of Nutrition Vol. 127 No. 1 January 1997, pp. 130–136), the entire content of which is hereby incorporated by reference.

Fiber Content

In a preferred embodiment the present method comprises the administration of a liquid composition comprising between 10 and 300 grams indigestible fiber per liter, preferably between 20 and 150 grams indigestible fiber per liter. Advantageously, the indigestible fiber is a water-soluble fiber. The use of water-soluble fiber provides a solution with acceptable transparency, which is believed to improve acceptance to the product.

Overweight

The term overweight as used in the present invention refers to a bodyweight and/or an adipose tissue mass that is above the desired bodyweight and/or desired adipose tissue mass. Obese monogastric mammals are considered overweight. Human subjects who have a body mass index above 25 most advantageously use the present method. The present method can thus suitably be used to reduce adipose tissue mass or prevent an increase in adipose tissue mass and to increase the ratio lean body mass to adipose tissue mass and/or the ratio muscle mass to adipose tissue mass.

The present method can both be used to treat or prevent overweight in therapy and/or for the cosmetic treatment or prevention of overweight, i.e. losing weight.

It was found that the present liquid composition can suitably be used to induce satiety, and thereby mimic and even exceed the satiety inducing effect of a sugar containing soft drink. Hence the present drink can be advantageously in a method for the reduction of the appetite in a human, said method comprising administering to said human an appetite reducing amount of the above described composition. The present method is preferably used to prevent or treat overweight in humans, even more preferably human adolescents.

Furthermore, the present composition reduces caloric intake of a meal when the drink is consumed shortly before or during the same meal. Hence the present invention also provides a method for reducing the caloric intake of a meal, for prevention of ingesting excess calories when ingesting a meal and/or controlling daily caloric intake, said method comprising administering to a human an effective amount of the liquid drink as described above, shortly before or during the meal (i.e. breakfast, brunch, lunch, high tea or dinner).

In a further preferred embodiment, the liquid composition comprises packaging, instructions and/or indicia which teach the use of liquid composition in association with weight loss. The indicia or instruction may be in any form, such as language directing the user towards the intended use, e.g. by providing the product with a name which points the consumer towards the intended use, such as by naming the product "slimwater", "low caloric drink", "leandrink". Also pictures or drawings may be used to direct the consumer towards the intended use, such as a slim figure or a balance. The indicia are preferably selected from the group consisting of alphabetic indicia, numeric indicia, color indicia, graphic indicia, and combinations thereof.

EXAMPLES

Example 1

Appetite Reducing Drink

A unit dosage of an appetite reducing drink containing:

| | |
|---|---|
| 320.1 ml | water; |
| 4.44 g | Genu ®pectin LM-104 AS-Z (Orffa Hercules); |
| 0.08 g | CaCO3; |
| 0.02 g | Na-saccharine; |
| 0.2 g | Na- cyclamate; |
| 0.02 g | Sucralose; |
| 0.016 g | Carrageenan; |

-continued

| | |
|---|---|
| 0.44 g | Peach-Orange flavor (Quest International); |
| 0.39 g | Soy masking (Givaudan); and |
| 0.005 g | T-PT8-WS yellow coloring agent (Chr. Hanssen). |

The product has a viscosity of 3.4 mPas at a shear rate of 100 s$^{-1}$ at pH 6.02 and at a temperature of 20° C., and a viscosity of at least 1000 mPas at a shear rate of 100 s$^{-1}$ at pH 3 and a temperature of 37° C. The caloric density of the product is about 21 kcal per liter.

Example 2

Satiety Inducing Effect of Present Drink.

The appetite suppressive effect and thirst quenching effect of the present drink was tested in humans. In acontrolled, blind, randomized cross over study, either one unit dosage of the drink described in example 1 (drink A), one unit dosage of a sugar containing drink (drink B) or one unit dosage of a low caloric drink (drink C) were administered (see Table 1 for ingredients of one unit dosage of the sugar-containing and low-caloric drink). Nine healthy volunteers participated in the study. Subjects ingesting medication that might affect appetite or satiety were excluded.

Subjects were randomly allocated to one of three study groups. Each group received drink A, B and C on three separate days, but in different order. Group 1 (n=3): drink A on day 1, drink B on day 2, and drink C on day 3; Group 2 (n=3): drink B on day 1, drink C on day 2, and drink A on day 3; Group 3 (n=3): drink C on day 1, drink A on day 2, and drink B on day 3. Appetite, satiety and thirst were assessed after ingestion of each of the drinks.

Subjects started a study morning after an overnight fast. They filled in a questionnaire about appetite, satiety and thirst at baseline (t=0). Subsequently, subjects consumed a unit dosage of drink A, B or C drink within 10 minutes. During the 3 hours after the first sip of a drink appetite, satiety and thirst were rated at 10, 20, 30, 45, 60, 90, 120, 150, 180 minutes. Participants were not allowed to eat or to consume any drinks in these three hours. This procedure was repeated with the two other drinks. Subjects were asked to perform comparable physical activity during the 3 measurement mornings.

TABLE 1

| | Drink B | Drink C |
|---|---|---|
| Water (tap) (ml) | 301 | 319.4 |
| Sucrose (g) | 29.3 | 0 |
| Aspartame (g) | 0 | 0.05 |
| Na- cyclamate (g) | 0 | 0.12 |
| MCC-91, Avicel RC591; Cloudifier (Caldic/Ferwo) (g) | 2.6 | 2.6 |
| Peach-Orange flavor (Quest Int.) (g) | 0.22 | 0.22 |
| T-PT8-WS yellow; coloring agent (g) (Chr. Hanssen). | 0.003 | 0.003 |
| Citric acid (g) | 1.0 | 1.1 |

Questionnaires

Scores for appetite, satiety and thirst were determined using visual analogue scales (VAS scores) from 100 mm by means of a slash on each labeled line. The term 'not at all' was placed at the left side and the term 'extremely' at the right side to score for each label.

Statistical Analysis

The averaged ratings are shown in FIGS. 1a, 2a, 3a and 4a. To determine differences in appetite, satiety and thirst quenching effect, the Area Under the Curve (AUC) for each question and each product was calculated. The GLM repeated measures test was used to determine differences in AUC between the three drinks. Statistical differences were assumed when p<0.05. FIGS. 1b, 2b, 3b and 4b show the AUC for each question and each product.

Results

Results are shown as mean±SEM.

'*' means significantly different from Drink C (p<0.05)

FIG. 1a show the average rating results given upon the question "Are you hungry". FIG. 1a shows a reduced hunger feeling after ingestion of Drink A compared to Drink C, almost immediately after ingestion of the drink. The "hunger feeling" after ingestion of Drink A is also reduced compared to the situation were drink B was consumed, particularly about 1 hour after ingestion of the drink.

FIG. 1b shows the AUC of the average rating results depicted in FIG. 1a. The significantly reduced AUC shows the appetite reducing effects of the present drink.

FIG. 2a shows the average rating results given on "Appetite for food". FIG. 2a shows a reduced appetite for food after ingestion of drink A compared to drink B and C, thus is indicative for the appetite reducing effect of the drink.

FIG. 2b shows the AUC of the average rating results depicted in FIG. 2a. The significantly reduced AUC shows the appetite reducing effects of the present drink.

FIG. 3a shows the average rating results given upon the question "How much could you eat". FIG. 3a shows that the average score after ingestion of drink A is lower than after ingestion of drink B or C. FIG. 3b shows the AUC of the average rating results depicted in FIG. 3a. The significantly reduced AUC shows the appetite reducing effects of the present drink.

FIG. 4a shows the average rating results given upon the question "Are you thirsty". FIG. 4a shows that the average score after ingestion of drink A is lower than after ingestion of drink B or C. FIG. 4b shows the AUC of the average rating results depicted in FIG. 4a. These results are indicative for the good thirst quenching properties of the present drink.

Example 3

Calcium Availability During Fermentation

| Preparation of MacFarlane medium | |
|---|---|
| Buffered peptone water | 3.0 g/l |
| Yeast Extract | 2.5 g/l |
| Tryptone | 3.0 g/l |
| L-Cysteine-HCl | 0.4 g/l |
| Bile salts | 0.05 g/l |
| $K_2HPO_4 \cdot 3H2O$ | 2.6 g/l |
| $NaHCO_3$ | 0.2 g/l |
| NaCl | 4.5 g/l |
| $MgSO_4 \cdot 7H_2O$ | 0.5 g/l |
| $CaCl_2$ | 0.228 g/l |
| $FeSO_4 \cdot 7H_2O$ | 0.005 g/l | pH was adjusted to 6.3±0.1 using 2M HCl and subsequently the medium was sterilized.

Preparation or Fecal Suspension:

Under anaerobic conditions, human feces were suspended in McFarlane medium in a weight ratio feces: MacFarlane medium of 1:5. The suspension was subsequently sieved to remove solid components.

Fermentation 15 ml of the fecal suspension was mixed with a dry mixture consisting of either pectin and calcium; or pectin, calcium and oligosaccharide (see Tabel 9) and incubated for 24 hours at 37° C. under anaerobic conditions. After incubation, the solids were removed from the suspension by centrifugation and pH and free calcium concentration were determined with a calcium electrode (model 720A, ThermoOrion, Beverly, USA). The results are given in Table 2.

TABLE 2

| Sample No | LM Pectin*** (mg) | $CaPO_4$ (mg) | Oligosaccharide | pH | Free calcium (ppm) |
|---|---|---|---|---|---|
| 1 | 100 | 100 | 500 mg Fibersol ®* | 4.6 | 200 |
| 2 | 100 | 100 | — | 5.5 | 107 |
| 3 | 200 | 100 | 320 mg Fibersol ®* | 4.6 | 180 |
| 4 | 200 | 100 | — | 5.3 | 144 |
| 5 | 50 | 100 | 250 mg FOS** | 3.9 | 362 |
| 6 | 50 | 100 | — | 5.7 | 86 |

*Fibersol-2 ® (Matsutani)
**Raftilose ™ (Orafti Active Food Ingredients)
***Genu-pectin LM-104 AS (Orffa-Hercules)

Example 4

A unit dosages of about 100 ml for use in a method for the prevention of overweight comprising:

0.55 gram 31% methoxylated, 17% amidated apple pectin 154 mg calcium carbonate 1 gram Fibersol 2 (Matsutani Chemical industry Co., Japan)

Filled up with water to 100 ml (pH adjusted to 7 with 10% KOH solution)

What is claimed is:

1. A method for the treatment and/or prevention of overweight in a monogastric mammal comprising drinking a liquid edible composition with a pH of more than 5, a viscosity below 50 mPas at a shear rate of 100 $s^{-1}$ and 20° C., and a viscosity of at least 125% of the aforementioned viscosity at a pH 3 and a temperature of 37° C.; and with a caloric density between 0 and 500 kcal per liter, the composition comprising:
   a. between 0.01 and 5 wt. % of one or more polysaccharides selected from the group consisting of pectin with a degree of methoxylation below 50% and alginate;
   b. between 0.01 and 3 wt. % calcium provide by a calcium salt with a solubility below 0.15 g per 100 ml water at 20 ° C. and pH 7.

2. The method according to claim 1, wherein the composition further comprises between 0.01 wt. % and 15 wt. % indigestible fermentable ingredient.

3. The method according to claim 2, wherein the indigestible fermentable ingredient is oligosaccharide and/or polyol.

4. The method according to claim 1, wherein the composition comprises between 10 and 150 grams water-soluble indigestible fermentable fiber per liter.

5. The method according to claim 1, wherein the liquid edible composition contains between 0 and 1 wt. % glycerides and/or fatty acids based on the total weight of the liquid composition.

6. The method according to claim 1, wherein the liquid edible composition further comprises a food grade flavor.

7. The method according to claim 1, wherein the liquid edible composition contains between 0 and 3 wt. % digestible carbohydrates based on the total weight of the liquid composition.

8. The method according to claim 1, wherein the liquid edible composition has a viscosity below 25 mPas at a shear rate of 100 $s^{-1}$ and 20° C., and a viscosity of at least 250 mPas at a shear rate of 100 $s^{-1}$ at pH 3 and at 37° C.

9. The method according to claim 1, wherein at least 96 wt. % of the liquid edible composition consists of pectin and/or alginate, calcium salt, water and, if present, indigestible fermentable ingredient.

10. The method according to claim 1, wherein the monogastric mammal is a human.

11. The method according to claim 1, comprising administering a unit dosage that contains between 50 and 2000 ml of the liquid composition.

12. The method according to claim 1, wherein the composition further comprises low caloric sweetener.

13. The method according to claim 1, wherein the liquid edible composition contains between 0.1 and 2.5 wt. % pectin.

14. A method for inducing satiety in a mammal, comprising administering to said mammal a liquid edible composition with a pH of more than 5, a viscosity below 50 mPas at a shear rate of $100 s^{-1}$ and 20° C., and a viscosity of at least 125% of the aforementioned viscosity at a pH 3 and a temperature of 37° C.; and with a caloric density between 0 and 50 kcal per liter, the composition comprising:
 a. between 0.01 and 5 wt. % of one or more polysaccharides selected from the group consisting of pectin with a degree of methoxylation below 50% and alginate;
 b. between 0.01 and 3 wt. % calcium provided by a calcium salt with a solubility below 0.15 g per 100 ml water at 20° C. and pH 7.

15. The method according to claim 14, wherein the composition further comprises between 0.01 wt. % and 15 wt. % indigestible fermentable ingredient.

16. The method according to claim 15, wherein the indigestible fermentable ingredient is oligosaccharide and/or polyol.

17. The method according to claim 14, wherein the composition comprises between 10 and 150 grams water-soluble indigestible fermentable fiber per liter.

18. The method according to claim 14, wherein the liquid edible composition contains between 0 and 1 wt. % glycerides and/or fatty acids based on the total weight of the liquid composition.

19. The method according to claim 14, wherein the liquid edible composition further comprises a food grade flavor.

20. The method according to claim 14, wherein the liquid edible composition contains between 0 and 3 wt. % digestible carbohydrates based on the total weight of the liquid composition.

* * * * *

UNITED STATES PATENT AND TRADEMARK OFFICE
CERTIFICATE OF CORRECTION

PATENT NO. : 6,989,166 B2  Page 1 of 1
APPLICATION NO. : 10/279968
DATED : January 24, 2006
INVENTOR(S) : Frederik Gerhard Johan Te Hennepe et al.

It is certified that error appears in the above-identified patent and that said Letters Patent is hereby corrected as shown below:

Column 16, line 2, change "50" to --500--.

Signed and Sealed this

Fifth Day of February, 2008

JON W. DUDAS
*Director of the United States Patent and Trademark Office*